(12) United States Patent
Shin et al.

(10) Patent No.: US 9,702,507 B2
(45) Date of Patent: Jul. 11, 2017

(54) DEVICE FOR CONTROLLING PARTICLES

(71) Applicant: KOREA INSTITUTE OF SCIENCE AND TECHNOLOGY, Seoul (KR)

(72) Inventors: Hyun Joon Shin, Seoul (KR); Jin Sik Kim, Incheon (KR)

(73) Assignee: Korea Institute of Science and Technology, Seoul (KR)

( * ) Notice: Subject to any disclaimer, the term of this patent is extended or adjusted under 35 U.S.C. 154(b) by 406 days.

(21) Appl. No.: 14/279,630

(22) Filed: May 16, 2014

(65) Prior Publication Data
US 2015/0041012 A1 Feb. 12, 2015

(30) Foreign Application Priority Data

Aug. 7, 2013 (KR) ........................ 10-2013-0093795

(51) Int. Cl.
*B01L 3/00* (2006.01)
*F17D 3/01* (2006.01)

(52) U.S. Cl.
CPC ........... *F17D 3/01* (2013.01); *Y10T 137/2082* (2015.04)

(58) Field of Classification Search
CPC ....................................................... B01L 3/00
USPC ........... 422/68.1, 81, 502, 503; 436/43, 174, 436/177, 180; 435/285.2; 204/547
See application file for complete search history.

(56) References Cited

U.S. PATENT DOCUMENTS

| | | | | |
|---|---|---|---|---|
| 5,106,468 A | * | 4/1992 | Chimenti | 204/564 |
| 5,454,472 A | * | 10/1995 | Benecke et al. | 209/127.1 |
| 5,671,086 A | * | 9/1997 | Parvin et al. | 359/391 |
| 6,149,789 A | * | 11/2000 | Benecke et al. | 204/547 |
| 2007/0125941 A1 | * | 6/2007 | Lee et al. | 250/251 |
| 2012/0088295 A1 | * | 4/2012 | Yasuda et al. | 435/288.7 |
| 2012/0298511 A1 | * | 11/2012 | Yamamoto | 204/602 |

FOREIGN PATENT DOCUMENTS

| JP | 9-79404 A | 3/1997 |
|---|---|---|
| KR | 10-2012-0041870 A | 5/2012 |

* cited by examiner

*Primary Examiner* — Brian J Sines
(74) *Attorney, Agent, or Firm* — NSIP Law (57) ABSTRACT

Provided is a particle control device for controlling fine particles. The particle control device includes: a base with a predetermined area and including an insulator; a first electrode and a second electrode disposed on the base such that they are separated from each other by a predetermined distance; and a fluid flow path disposed on the base so as to pass between the first electrode and the second electrode and to allow a solution to flow. The first electrode includes a plurality of branch electrodes with fine widths, each branch electrode having one end that is adjacent to the second electrode, with the fluid flow path interposed between the branch electrode and the second electrode.

10 Claims, 6 Drawing Sheets

DEVICE FOR CONTROLLING PARTICLES

RELATED APPLICATIONS

This application claims the benefit of Korean Patent Application No. 10-2013-0093795, filed on Aug. 7, 2013, in the Korean Intellectual Property Office, the disclosure of which is incorporated herein in its entirety by reference.

BACKGROUND

1. Field

One or more embodiments of the present invention relate to a device for controlling particles, and more particularly, to a particle control device for controlling fine particles, including: a base; first and second electrodes disposed on the base such that they are separated from each other by a predetermined distance; and a fluid flow path that passes between the first and second electrodes and allows a solution to flow, wherein the first electrode has a plurality of branch electrodes having fine widths, each branch electrode having one end that is adjacent to the second electrode, with the fluid flow path interposed between the branch electrode and the second electrode, and wherein the fine particles are controlled due to a dielectrophoretic force between the first and second electrodes by applying powers having different polarities to the first and second electrodes.

2. Description of the Related Art

High-precision devices such as semiconductors, high-precision equipment such as nano-machines, or various medical fields involve micro- to nano-sized high-precision operation.

To overcome limitations of current semiconductor technology, research has been actively conducted to develop integration circuits and optical devices using different media. Among these, plasmon-based devices have attracted much attention. The main focus of realizing practical plasmon-based devices lies in a technology of arranging nanoparticles such as quantum dots that emit light and metal nanowires that can guide light at desired positions.

Various devices have been developed to precisely manipulate or control nanoscale and fine particles in a predetermined solution for analysis or other processings. Recently, a method of controlling particles by using the behavior of particles undergoing a dielectrophoretic force has been commonly used. According to the method, the dielectrophoretic force is applied to a polarizable particle in a non-uniform electric field.

The method of controlling particles by using a dielectrophoretic force is receiving considerable attention since it allows high precision manipulation and control of fine particles.

Thus, appropriate exploitation of a dielectrophoretic force remains the major challenge in the development of devices for controlling particles and various industrial applications related to the devices.

SUMMARY

One or more embodiments of the present invention include a particle control device for controlling fine particles, including: a base; first and second electrodes disposed on the base such that they are separated from each other by a predetermined distance; and a fluid flow path that passes between the first and second electrodes and allows a solution to flow, wherein the first electrode has a plurality of branch electrodes having fine widths, each branch electrode having one end that is adjacent to the second electrode, with the fluid flow path interposed between the one end and the second electrode, and wherein the fine particles that are between the first electrode and the second electrode are controlled due to a dielectrophoretic force between the first and second electrodes by applying powers having different polarities to the first and second electrodes.

Additional aspects will be set forth in part in the description which follows and, in part, will be apparent from the description, or may be learned by practice of the presented embodiments.

According to one or more embodiments of the present invention, a particle control device for controlling fine particles includes: a base with a predetermined area and including an insulator; a first electrode and a second electrode disposed on the base such that they are separated from each other by a predetermined distance; and a fluid flow path disposed on the base so as to pass between the first electrode and the second electrode and allow a solution to flow. The first electrode includes a plurality of branch electrodes with fine widths, each branch electrode having one end that is adjacent to the second electrode, with the fluid flow path interposed between the branch electrode and the second electrode. The fine particles that are between the first electrode and the second electrode are controlled due to a dielectrophoretic force between the first electrode and the second electrode by applying powers having different polarities to the first electrode and the second electrode.

The first electrode and the second electrode may be separated from each other in a horizontal direction on a plane created by the base.

The base may include a solution filling groove formed on the fluid flow path between the first electrode and the second electrode, and at least a portion of the end of each of the branch electrodes may be disposed on the solution filling groove.

The particle control device may further include a cover glass disposed on the base and having a predetermined area, wherein the fluid flow path is formed by a space between an upper surface of the base and the cover glass.

At least some of the plurality of branch electrodes may be bent or curved so that their ends that are adjacent to the second electrode are densely arranged towards the second electrode.

Each of the branch electrodes may include a tip at the end that is adjacent to the second electrode, and the tip may have a fine width and shaped like a pin that extends towards the second electrode.

The width of the tip may be in a range of about 1 nm to about 100 nm.

According to one or more embodiments of the present invention, a particle control device for controlling fine particles includes: a base including an insulator; a lower electrode having at least a portion buried in the base; and an upper electrode disposed on the lower electrode and separated from the lower electrode by a predetermined distance in a longitudinal direction, wherein the lower electrode includes a plurality of branch electrodes with fine widths, each branch electrode having one end that is adjacent to the upper electrode, and wherein the fine particles that are between the first electrode and the second electrode are controlled due to a dielectrophoretic force between the upper electrode and the lower electrode by applying powers having different polarities to the upper electrode and the lower electrode The upper electrode may be formed of a material having light transmittance and electrical conductivity.

The particle control device may further include a fluid flow path configured to pass between the upper electrode and the lower electrode and allow a solution to flow. The fluid flow path may be formed by a space between the upper electrode and the lower electrode.

According to the particle control device, the first electrode having a plurality of branch electrodes and the second electrode are disposed adjacent to each other, and a fluid flow path is created between the first and second electrodes so as to allow a solution having predetermined particles to flow. Particles may be controlled by a dielectrophoretic force between the first and second electrodes by applying powers having different polarities to the first and second electrodes.

A predetermined fluid flow path may be created between the first and second electrodes. A hydrophilic coating layer is disposed inside the fluid flow path while a hydrophobic coating layer is disposed outside the fluid flow path, thereby allowing the solution to flow toward the inside of the fluid flow path having high hydrophilic property. Thus, the flow of the solution is accelerated, and particle control efficiency may be improved.

The branch electrode may have a tip with a fine width and an elongated length at an end thereof that is adjacent to the second electrode. In other words, the branch electrode has a tip elongated into a thin pin form at the end thereof, and the tip is disposed proximate the second electrode. The configuration facilitates fabrication and processing of the branch electrode and achieves concentration and enhancement of a dielectrophoretic force through the tip.

A solution filling groove including a recess is formed in the base on which the fluid flow path is formed so as to slow down for a moment the flow of the solution along the fluid flow path and capture the solution, thereby facilitating control of particles in the solution.

The device may further include a cover glass having a predetermined area disposed on the base. The fluid flow path is formed by a gap between an upper surface of the base and the cover glass. That is, the gap is formed simply by arranging the cover glass and is used as the fluid flow path along which the solution flows, thereby eliminating the need for forming a separate fluid flow path. Furthermore, a capillary action is caused by the gap between the cover glass and the upper surface of the base and facilitates flow of the solution, thereby eliminating the need for a separate manipulation or device for circulating the solution and allowing simple and affordable particle control.

In addition, since particle control occurs in a nano-sized electrode, particle control may be performed at a single particle level. After control of the particles, the particles may be observed and then subjected to a subsequent reaction to redischarge into the fluid flow path. Control of particles at the single particle level may be a fundamental technology in biological research involving analysis of single proteins and DNA and new semiconductor processes.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. These embodiments are provided so that this disclosure will be thorough and complete and will fully convey the exemplary embodiments to those of ordinary skill in the art. The scope of the present invention is defined by the following claims.

Spatially relative terms, such as "below," "beneath," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented, and the spatially relative descriptors used herein may be interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated components, steps, operations, and/or elements, but do not preclude the presence or addition of one or more other components, steps, operations, and/or elements.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein. As used herein, the term "and/or" includes any and all combinations of one or more of the associated listed items. Expressions such as "at least one of," when preceding a list of elements, modify the entire list of elements and do not modify the individual elements of the list.

In the drawings, thicknesses or sizes of elements are exaggerated, omitted, or schematically illustrated for convenience of explanation and clarity. A size or area of each element does not entirely reflect an actual size or area thereof.

Angles or directions used to describe structures of the present invention are based on those shown in the drawings. Unless a reference point of an angle or angular positional relations in the structures of the present invention are clearly described, the related drawings may be referred to.

Figure 1:
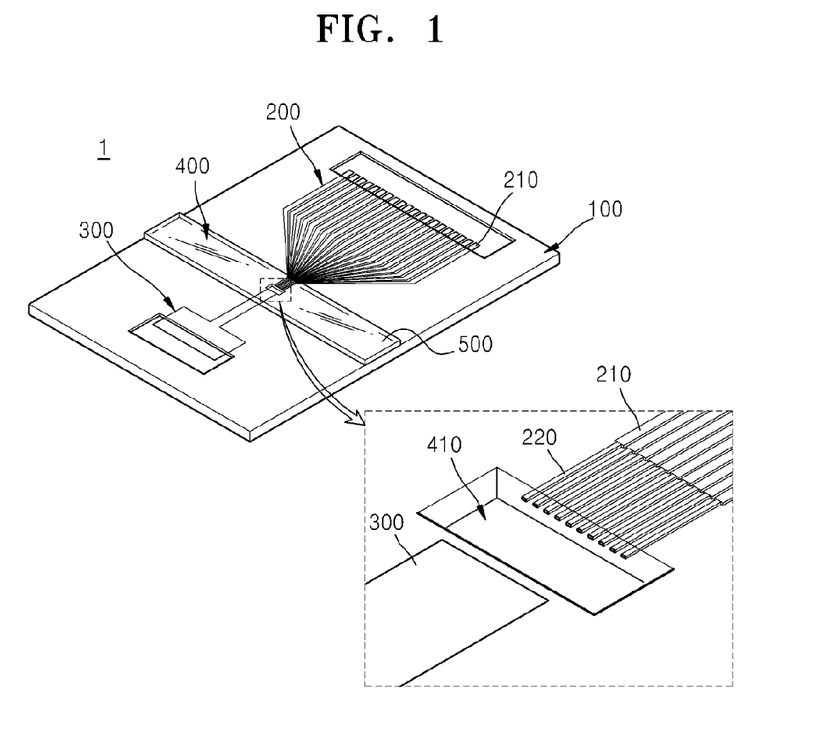
FIG. 1 illustrates a particle control device according to an exemplary embodiment of the present invention.
Figure 2:
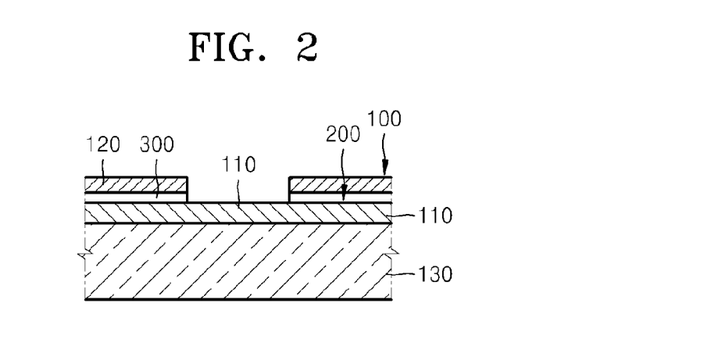
FIG. 2 is a cross-sectional view of a portion of the particle control device of FIG. 1.
Figure 3:
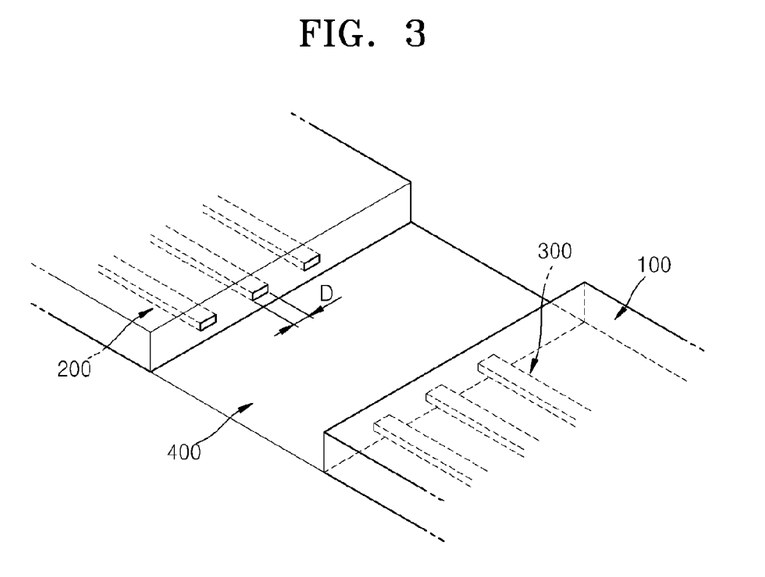
FIG. 3 illustrates a structure of a portion of the particle control device of FIG. 1.
Figure 4:
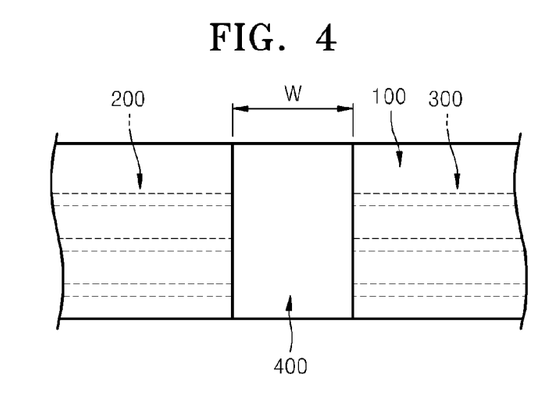
FIG. 4 illustrates a cross-sectional view of the structure of FIG. 3.

FIG. 1 illustrates a particle control device 1 according to an exemplary embodiment of the present invention. FIG. 2 is a cross-sectional view of a portion of the particle control device 1. FIG. 3 illustrates a structure of a portion of the particle control device 1. FIG. 4 illustrates a cross-sectional view of the structure of FIG. 3.

The particle control device 1 according to the present embodiment controls fine particles. The particle control device 1 includes a base 100 with a predetermined area and including an insulator, first and second electrodes 200 and 300 disposed on the base 100 such that they are separated from each other by a predetermined distance, and a fluid flow path 400 that is disposed on the base 100 so as to pass between the first and second electrodes 200 and 300 and allows a solution to flow. The first electrode 200 includes a plurality of branch electrodes 210 having fine widths, each having one end disposed adjacent to the second electrode 300, with the fluid flow path 400 interposed between the one end and the second electrode 300. In addition, by applying powers having different polarities to the first and second electrodes 200 and 300, respectively, particles are controlled by using a dielectrophoretic force between the first and second electrodes 200 and 300.

The base 100 is constructed by a substrate having predetermined area and thickness and may be formed of an insulating material so as not to affect the generation of an electric field by the first and second electrodes 200 and 300. The base 100 may be also formed of a material with good processability so as to facilitate a fabrication step such as partial etching. For example, the base 100 may be formed from a silicon wafer having predetermined thickness and area, and fabricated by a silicon wafer processing. The base 100 may have a structure suitable for its usage and purpose, and is not limited to the structure shown in FIGS. 1 through 4.

The first and second electrodes 200 and 300 are disposed on the base 100, which may mean that they are disposed not only on an upper surface of the base 100 but also in the base 100 so as to form a layer having a predetermined thickness, as shown in FIG. 1.

The first and second electrodes 200 and 300 each may be formed of a material selected from the group consisting of various conductive materials, e.g., metals such as aluminum (Al), gold (Au), platinum (Pt), copper (Cu), silver (Ag), tungsten (W), and titanium (Ti), metal oxides such as indium tin oxide (ITO) and tin oxide ($SnO_2$), conductive plastics, and metal impregnated polymer, but the present invention is not limited thereto. The first and second electrodes 200 and 300 may be formed of Au that is resistant to corrosion.

The first and second electrodes 200 and 300 are connected to positive and negative terminals, respectively. The first and second electrodes 200 and 300 are separated from each other to create a non-uniform electric field upon application of power. In the present embodiment, the first and second electrodes 200 and 300 may be disposed on a plane created by the base 100 and separated from each other in a horizontal direction. However, in another embodiment as described below, they are disposed on the base 100 and separated from each other in a longitudinal direction.

The fluid flow path 400 may be formed between the first and second electrodes 200 and 300 so as to allow a solution containing predetermined particles to flow.

The fluid flow path 400 as a passage through which the circulating solution flows may be an independent element, but is not limited thereto. For example, the fluid flow path 400 may be constructed by a groove formed in the base 100 or a space between the base 100 and another element. Although FIG. 1 does not illustrate the fluid flow path 400 in detail, the fluid flow path 400 may be configured in various shapes.

When the fluid flow path 400 is a predetermined groove formed in the base 100, the solution may flow through the groove.

Furthermore, the fluid flow path 400 may be configured to accelerate the flow of the solution. In one embodiment, a coating layer is formed on the base 100 and includes a hydrophilic coating layer 110 and/or a hydrophobic coating layer 120. For example, the hydrophilic coating layer 110 may be formed on the base 100, and the hydrophobic coating layer 120 may be formed on the hydrophilic coating layer 110. The hydrophilic coating layer 110 and the hydrophobic coating layer 120 may be each formed by depositing a material having a predetermined thickness on the base 100, but they are not limited thereto. A foundation part 13 is disposed below the hydrophilic coating layer 110 to form a foundation for the base 100.

The hydrophilic coating layer 110 is made of a material having higher hydrophilic property than the hydrophobic coating layer 120, such as silicon oxide ($SiO_2$). The hydrophilic coating layer 110 is formed on the base 100, and in particular, between the hydrophobic coating layer 120 and the base 100.

The hydrophobic coating layer 120 is formed of a material having lower hydrophilic property than the hydrophilic coating layer 110, such as silicon nitride ($Si_3N_4$). The hydrophobic coating layer 120 is formed on the hydrophilic coating layer 110 to form an upper surface of the base 100.

The hydrophobic coating layer 120 on a portion of the base 100 corresponding to the fluid flow path 400 may be partially etched to expose the hydrophilic coating layer 110 in the fluid flow path 400. Thus, the hydrophilic coating layer 110 is exposed in the fluid flow path 400, while the hydrophobic coating layer 120 is formed outside the fluid flow path 400.

In other words, the fluid flow path 400 may be a groove by which the hydrophilic coating layer is exposed. The hydrophilic coating layer 110 is formed in the fluid flow path 400 through which the solution as a sample flows, and the hydrophobic coating layer 120 is formed outside of the fluid flow path 400, thereby facilitating the flow of the solution.

In detail, the hydrophilic coating layer 110 and the hydrophobic coating layer 120 are disposed inside and outside the fluid flow path 400, respectively, thereby inducing the flow of the solution toward the inside of the fluid flow path 400 having high hydrophilic property. Thus, the circulation of the solution is accelerated, and particle control efficiency may be improved.

The first electrode 200 may include a plurality of branch electrodes 210 with fine widths, each branch electrode 210 having one end disposed adjacent to the second electrode 300, with the fluid flow path 400 interposed between the one end and the second electrode 300.

That is, referring to FIG. 1, the first electrode 200 includes a group of the plurality of branch electrodes 210 having fine widths and a predetermined length. One end of each of the branch electrodes 210 extends toward and is disposed proximate the second electrode 300, with the fluid flow path 400 interposed therebetween.

In this case, the other end of each of the branch electrodes 210 may be connected to a single electrode pad or may be electrically connected thereto via another electrode. Furthermore, the second electrode 300 may be a single electrode pad, but is not limited thereto.

As shown in FIG. 3, like the first electrode 200, the second electrode 300 may also include a plurality of branch electrodes.

Referring to FIGS. 3 and 4, the first electrode 200 is separated from the second electrode 300 by a distance W. The branch electrode 210 has a predetermined width D.

By applying powers of different polarities to the first and second electrodes 200 and 300, particles are controlled by means of a dielectrophoretic force between the first and second electrodes 200 and 300.

Figure 5:
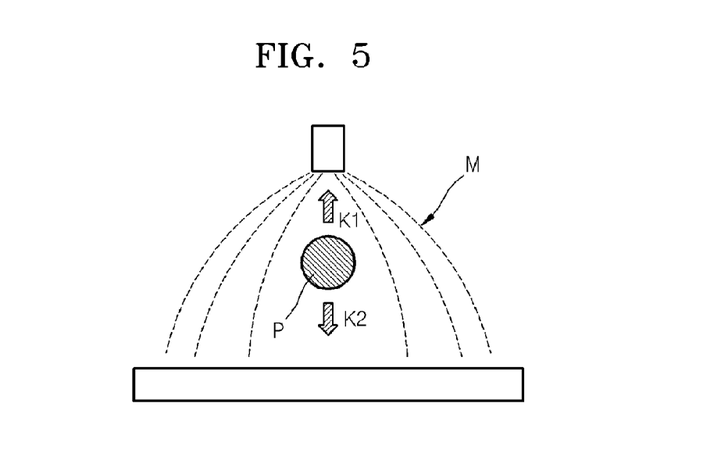
FIG. 5 illustrates the principle of dielectrophoresis used in a particle control device, according to an exemplary embodiment of the present invention.

FIG. 5 illustrates the principle of dielectrophoresis used in the particle control device 1, according to an exemplary embodiment of the present invention. Dielectrophoresis is a phenomenon in which when a polarizable particle P in a non-uniform electric field M is attracted toward a region of a high electric field gradient or a region of a low electric field gradient. When the polarizable particle P moves toward the region of a high electric field gradient, it is referred to as a positive DEP. When the polarizable particle P moves toward the region of a low electric field gradient, it is referred to as a negative DEP. The magnitude of a force exerted on the polarizable particle P by dielectrophoresis depends on a volume and dielectric properties of the polarizable particle P. Thus, according to the dielectrophoretic properties of the polarizable particle P, the polarizable particle P may move in a predetermined direction within the non-uniform electric field M, or may be trapped at a location in the non-uniform electric field M. For example, when particles exhibiting a positive DEP are mixed with particles exhibiting a negative DEP, it is possible to control a mixture of particles based on the dielectrophoresis phenomenon.

As described above, in the particle control device 1 according to the present embodiment, the first electrode 200, including the plurality of branch electrodes 210, is disposed adjacent to the second electrode 300, and the fluid flow path 400 is created between the first and second electrodes 200 and 300 so as to allow the flow of a solution having predetermined particles. By applying powers having different polarities to the first and second electrodes 200 and 300, respectively, particles may be controlled by using a dielectrophoretic force between the first and second electrodes 200 and 300.

While the particle control device 1 allows control of particles in the solution, the present invention is not limited thereto. For example, the particle control device 1 may control particles under any other conditions as well as the particles in the solution.

At least some of the branch electrodes 210 may be bent or curved so that their ends that are adjacent to the second electrode 300 are densely arranged.

That is, the dielectrophoretic force is concentrated at a predetermined portion, and the ends of the branch electrodes 210 are arranged densely at the predetermined portion so as to facilitate control of particles experiencing the dielectrophoretic force. Thus, as shown in FIG. 1, the second electrode 300 is an electrode pad including a projection with a small width, and the branch electrodes 210 are bent in a predetermined direction to extend toward the projection of the second electrode 300. In addition, as shown in FIG. 3, the second electrode 300 may also include a plurality of branch electrodes.

The above-described configuration allows the dielectrophoretic force to concentrate at a predetermined portion and facilitates control of particles.

Each of the branch electrodes 210 may have a tip 220 at an end thereof that is adjacent to the second electrode 300, and the tip 220 has a fine width and is shaped like a pin that extends toward the second electrode 300.

Figure 6:
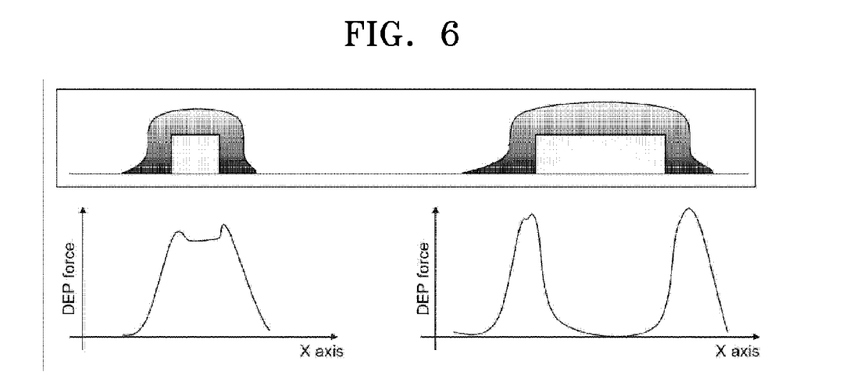
FIG. 6 illustrates a dielectrophoresis gradient according to the type of electrode, according to an exemplary embodiment of the present invention.

FIG. 6 illustrates a dielectrophoretic force gradient according to the type of electrode, according to an exemplary embodiment of the present invention.

Referring to FIG. 6, when a small area electrode having a small width of less than 100 nm is used, a dielectrophoretic force at a single point, because the dielectrophoretic force is generated due to a rapid change in an electric field at both edges of the electrode. Thus, when a large area electrode having a large width of greater than 100 nm is used, a dielectrophoretic force may be generated at two points, and be not exerted on some area upon release thereof. Furthermore, since the dielectric force is divided into two forces, it has a small magnitude. Thus, to achieve capturing and emission of particles, a small width electrode of less than 100 nm may be used.

Figure 7:
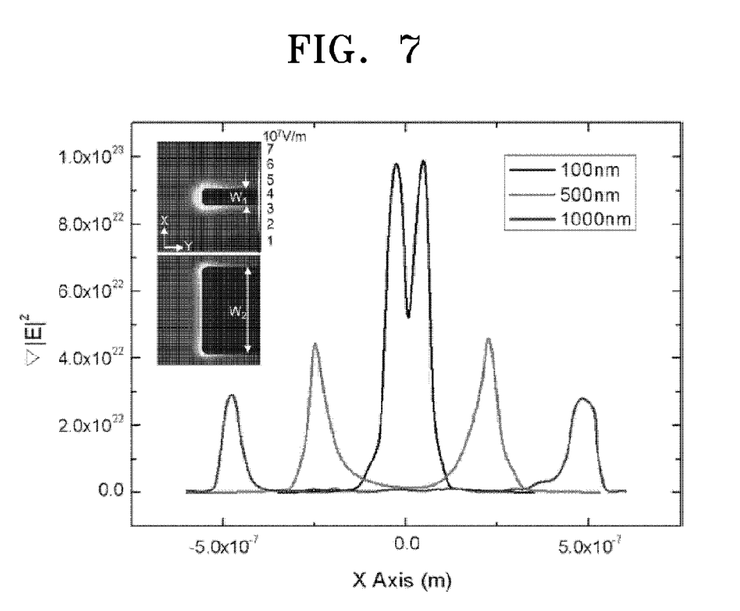
FIG. 7 is a graph illustrating the result of a simulation using COMSOL Multiphysics.

FIG. 7 is a graph illustrating the result of a simulation using COMSOL Multiphysics. A dielectrophoretic force may be defined by Equation (1) below:

$$\vec{F}_{DEP} = 2\pi r^3 \varepsilon_m \mathrm{Re}\left(\frac{\varepsilon_p^* - \varepsilon_m^*}{\varepsilon_p^* + \varepsilon_m^*}\right) \nabla |\vec{E}|^2 \quad (1)$$

Since the dielectrophoretic force is proportional to the product of an electric field and an electric field gradient, the result of a simulation shows the magnitude of $\nabla |\vec{E}|^2$ for a width of an electrode. As described above, when the area of an electrode is large, the dielectrophoretic force is divided into two forces and has a small magnitude.

Thus, as shown in FIG. 1, the branch electrode 210 may have the tip 220 with a fine width and an elongated length at an end thereof that is adjacent to the second electrode 300. In other words, the branch electrode 210 has the tip 220 elongated into a thin pin form at the end thereof, and the tip 220 is disposed proximate the second electrode. The above configuration facilitates fabrication and processing of the branch electrode 210 and achieves concentration and enhancement of a dielectrophoretic force through the tip 220.

As described above, when the width D of the tip 220 is extremely large, it is difficult to achieve concentration of a dielectrophoretic force. On the other hand, when the width D of the tip 220 is extremely small, the tip 220 may be damaged due to the circulation of a solution, or may be difficult to fabricate. Thus, the tip 220 may have a width D of several nm to several hundred nm, e.g., the width D ranging from 1 nm to 100 nm.

The base 100 may include a solution filling groove 410 formed on a fluid flow path 400 between the first and second electrodes 200 and 300. At least a portion of one end of each of the branch electrodes 210 is disposed on the solution filling groove 410.

That is, as shown in FIG. 1, the solution filling groove 410, including a recess, may be formed in the base 100 on which the fluid flow path 400 is formed. The solution filling groove 410 has a predetermined depth so as to slow down for a moment the flow of the solution along the fluid flow path 400 and capture the solution.

In this case, at least a portion of one end of each of the branch electrodes 210 may be disposed on the solution filling groove 410. In other words, a region where the projection of the second electrode 300 is adjacent to the tip 220 of the branch electrode 210 may overlap a portion of the base 100 corresponding to the solution filling groove 410. Due to this configuration, a dielectrophoretic force between the first and second electrodes 200 and 300 is exerted intensively on the solution filled in the solution filling groove 410, thereby facilitating control of particles in the solution. Furthermore, as described above, this configuration may slow down for a moment the flow of the solution along the fluid flow path and capture the solution, thereby further facilitating control of particles in the solution.

The particle control device 1 further includes a cover glass 500 having a predetermined area disposed on the base 100. The fluid flow path 400 is formed by a space between the upper surface of the base 100 and the cover glass 500.

The cover glass 500 may be formed of a material having a predetermined area and a relatively smooth surface. For example, the cover glass 500 may be formed of glass having light transmittance, but is not limited thereto.

The cover glass 500 may be disposed on the base 100 and separated from the base 100 by a distance. Thus, a fine gap is formed between the cover glass 500 and the base 100. In this case, a support may be disposed to create a space between the cover glass 500 and the base 100, but the present invention is not limited thereto. The particle control device 100 may further include a structure for adjusting the distance between the cover glass 500 and the base 100, but the present invention is not limited thereto.

The fluid flow path 400 may be formed by a space between the upper surface of the base 100 and the cover glass 500. In other words, a solution may flow through the space (i.e., a gap) between the cover glass 500 and the base 100, and thus the fluid flow path may be formed by the space. Thus, at least portions of the ends of the first and second electrodes 200 and 300 may be disposed between the cover glass 500 and the base 100, but the present invention is not limited thereto.

A described above, the fluid flow path 400 is formed by the gap between the cover glass 500 and the base 100. The gap may be formed simply by arranging the cover glass 500 and used as the fluid flow path 400 along which the solution flows, thereby eliminating the need for forming a separate fluid flow path 400. Furthermore, a capillary action is caused by the gap between the cover glass 500 and the base 100 and facilitates flow of the solution, thereby eliminating the need for a separate manipulation or device for circulating the solution and thus allowing simple and affordable particle control.

Figure 8:
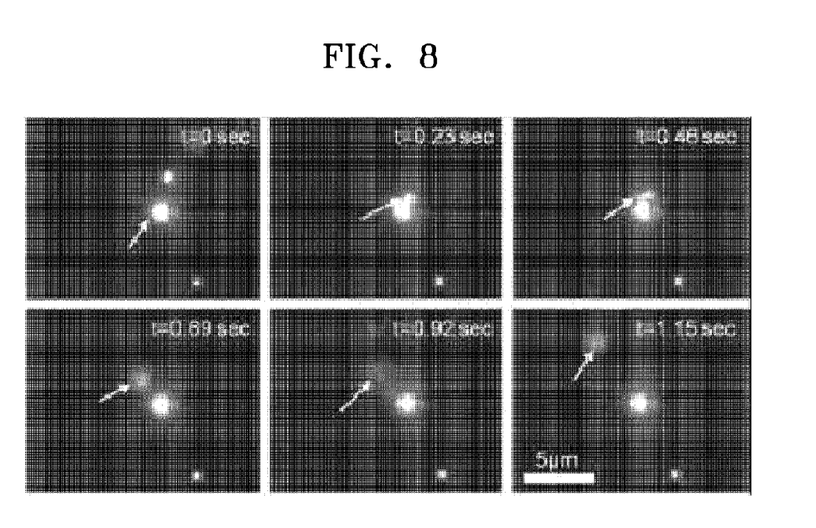
FIG. 8 illustrates pictures illustrating emission of a single nanoparticle from a nanoparticle agglomerate at a distal end of an electrode over time.
Figure 9:
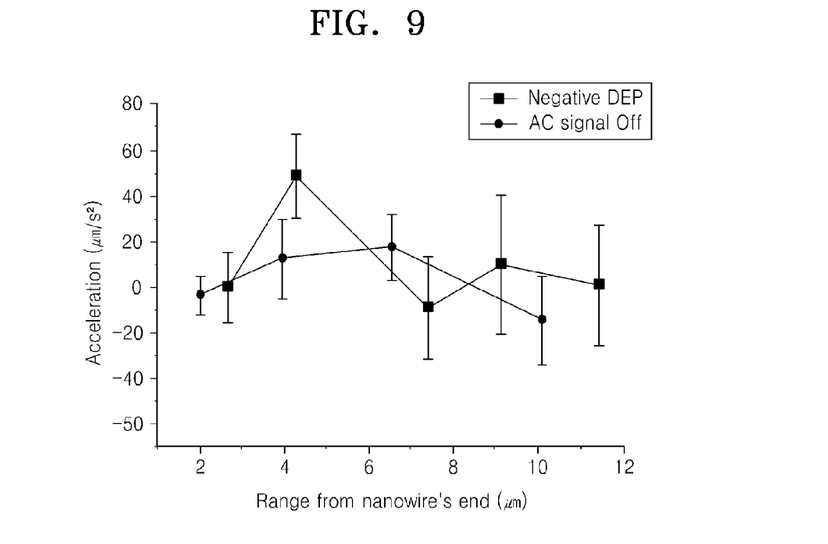
FIG. 9 illustrates a comparison between acceleration of a nanoparticle under an emission condition by using a negative dielectrophoretic force and that of a nanoparticle accidentally released by simply removing a force used to capture the nanoparticle.

FIGS. 8 and 9 illustrate the results of experiments performed by the particle control device 1.

FIG. 8 illustrates pictures illustrating emission of a single nanoparticle from a nanoparticle agglomerate at a distal end of an electrode over time. FIG. 9 illustrates a comparison between acceleration of a nanoparticle under an emission condition by using a negative dielectrophoretic force and that of a nanoparticle accidentally released by simply removing a force exerted to capture the nanoparticle.

In the experiment, as shown in FIG. 8, after many nanoparticles were intentionally attached to an electrode, movements of the nanoparticles that were detached one-by-one from the electrode were observed to identify a range and a region on which a force is exerted. Since it is quite difficult to observe movements of nanoparticles that were captured after being moved freely, the nanoparticles were attached to the electrode and then detached therefrom for observation. Since an electric field acts on the same region upon capturing and emission of particles, the experiments may show the same result.

As apparent from the result shown in FIG. 8, strong acceleration occurred within a range of 4 um from a distal end of the nano-sized electrode, which means that a negative dielectrophoretic force is exerted on a small region having a size of 4 um. Due to the strong force generated locally, it is possible to manipulate nanoparticles at the single particle level. Thus, the result of the experiment shows that precise manipulation and control of nanoparticles are possible according to embodiments of the present invention.

By adjusting a distance between the first and second electrodes 200 and 300, the intensity of an electric field may be controlled, thereby allowing appropriate control of particles. In one embodiment, when a displacement of an electrode is performed by a control device or driver, the distance between the first and second electrodes 200 and 300 may be adjusted, and appropriate control of particles may be selectively achieved.

Furthermore, by controlling the polarity of power that is applied to the first and second electrodes 200 and 300, reversible control may be achieved. That is, since particles may be attached or detached by controlling application of positive or negative powers, the movement of particles may be precisely controlled. In addition, particles may be controlled at single molecule level over a two-dimensional (2D) area.

A method of manufacturing the particle control device 1 according to the present embodiment will now be described.

First, to manufacture the first electrode 200 and the second electrode 300, electrodes are patterned by using electron beam lithography, and metals are deposited and patterned by using a lift-off process. Alternatively, metal nanowires formed chemical self-growth may be arranged at desired positions by light capturing or plasmon capturing.

An insulating material may be formed on the first and second electrodes 200 and 300 by using a deposition technique. The insulating material may be silicon oxide, silicon nitride, or other insulating polymer.

To adjust the distance between the first and second electrodes 200 and 300, an etching method such as reactive ion etching (RIE), inductively coupled plasma RIE (ICP-RIE), or oxide wet etching may be employed. When electrodes are arranged in a longitudinal direction as described below, the electrodes made of ITO may overlap one another to create the gap therebetween, but the present invention is not limited thereto.

The particle control device 1 may be used as described below.

Nanoparticles contained in a liquid medium are injected in the vicinity of the first and second electrodes 200 and 300, and power is applied to the first and second electrodes 200 and 300. The nanoparticles near the first and second electrodes 200 and 300 are attached to the first and second electrodes 200 and 300 due to a positive dielectrophoretic force. The positive dielectrophoretic force is generated due to a strong electric field created between the first and second electrodes 200 and 300 by applying alternating current (AC) and direct current (DC) powers thereto. In this case, the number of nanoparticles attached to the first and second electrodes 200 and 300 may be determined in proportion to the concentration of the nanoparticles and the magnitude of the dielectrophoretic force between the first and second electrodes 200 and 300. If reaction with unwanted nanoparticles occurs, the unwanted nanoparticles may be detached by using a negative dielectrophoretic force, thereby causing another reaction to take place.

Figure 10:
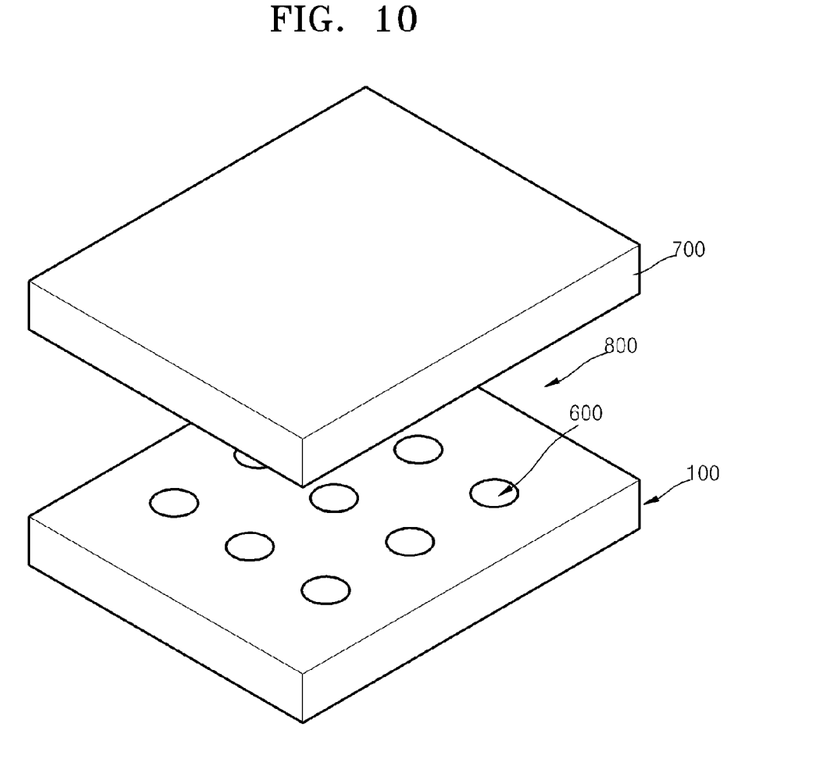
FIG. 10 illustrates a particle control device according to another exemplary embodiment of the present invention.
Figure 11:
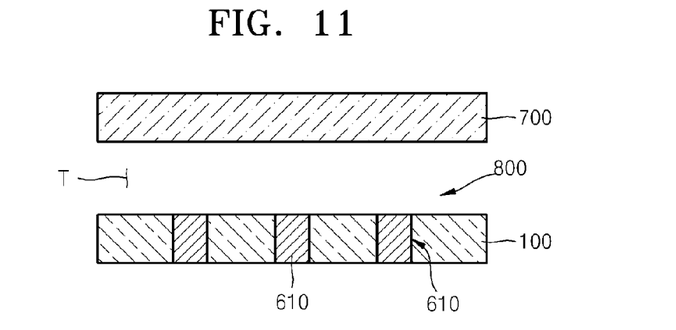
FIG. 11 is a cross-sectional view of the particle control device of FIG. 10.

FIG. 10 illustrates a particle control device according to another exemplary embodiment of the present invention. FIG. 11 is a cross-sectional view of the particle control device of FIG. 10

The particle control device according to the present embodiment includes a base 100 including an insulator, a lower electrode 600 with at least a portion thereof being buried in the base 100, and an upper electrode 700 disposed on the lower electrode 600 and separated from the lower electrode 600 by a distance. The lower electrode 600 includes a plurality of branch electrodes 610 with fine widths, each branch electrode 610 having one end that is adjacent to the upper electrode 700.

The base 100 may be formed of an electrical insulation material and may be configured in the same way as described above.

At least a portion of the lower electrode 600 is buried in the base 100. That is, referring to FIG. 10, the electrode 600 may be inserted and buried into the base 100.

The lower electrode 600 may include the plurality of branch electrodes 610 with fine widths. Like the branch electrodes 210, each of the branch electrodes 610 has a fine width and an elongated length. However, the branch electrode 610 is different from the branch electrode 210 in that the lower electrode 600 is embedded and buried in the base 600, and each of the branch electrodes 610 extends in a longitudinal direction. In this case, an upper end of the branch electrode 610 is exposed on the base 100, but is not limited thereto.

The upper electrode 700 may be disposed on the base 100 and separated from the lower electrode 600 by a distance. Thus, the end of the branch electrode 610 is separated from the upper electrode 700 by the distance. The upper electrode 700 may be an electrode pad having a predetermined area and cover a region having a predetermined area where the plurality of branch electrodes 610 are arranged.

A fluid flow path 800 may be formed between the base 100 and the upper electrode 700. Since the upper electrode 700 is disposed on the base 100 and the lower electrode 600 and separated therefrom by the distance, a gap T having a predetermined gap may be created between the base 100 and the upper electrode 700 and may define the fluid flow path 800 through which a solution flows.

That is, as described above with reference to the previous embodiment, a capillary action may be caused by the gap T between the base 100 and the upper electrode 700 and allow the solution to flow, thereby eliminating the need for a separate device or structure for circulating the solution between the upper electrode 700 and the lower electrode 600. The particle control device according to the present embodiment is different from the particle control device 1 in that the upper electrode 700 and the lower electrode 600 are arranged in the longitudinal direction, and the upper electrode 700 replaces the cover glass 500 in the particle control device 1.

Like in the particle control device 1, a coating layer is formed on the base 100 and includes a hydrophilic coating layer and a hydrophobic coating layer. For example, the hydrophilic coating layer may be formed on a portion where the lower electrode 600 is disposed, and the hydrophobic coating layer may be formed on the remaining portion, thereby allowing concentration of the solution in the portion where the lower electrode 600 is disposed. However, the present invention is not limited thereto. Furthermore, like in the particle control device 1, the branch electrodes 610 of the lower electrode 600 may be bent so that they are densely arranged at a predetermined region, and each of the branch electrodes 610 may have a tip.

The upper electrode 700 may be formed of a material having light transmittance and electrical conductivity.

For example, the upper electrode 700 may be formed of ITO, carbon nanotubes (CNT), or a transparent electrode material such as $SnO_2$ or indium zinc oxide (IZO), but is not limited thereto.

In the particle control device according to the present embodiment, electrical field gradients are created in the longitudinal direction, thereby facilitating capturing of particles by dielectrophoretic force. Furthermore, when the particle control device includes a component for adjusting a distance between the upper electrode 700 and the base 100, a dielectrophoretic force may be easily controlled by simply adjusting a height of the upper electrode 700, thereby facilitating control of particles.

Particle control devices according to embodiments of the present invention allow precise control of particles. The particle control devices may be used in various technologies including plasmon-based devices. To overcome limitations of current semiconductor technology, research has been actively conducted to develop integration circuits and optical devices using different media. Among these, plasmon-based devices have attracted the most attention. The main challenge of realizing practical plasmon-based devices lies in a technology of arranging nanoparticles such as quantum dots that emit light and metal nanowires that can guide light at desired positions. Thus, the particle control devices, which are configured to arrange nanoparticles on the electrodes at the single molecule level, may be used in realizing plasmonic devices. Furthermore, the particle control devices may be used in fields requiring nanoparticles exhibiting good performance formed by chemical self-growth, such as lasers utilizing quantum dots fabricated with epitaxial growth and dye-sensitized solar cells, to allow high yield arrangement of nanoparticles, thereby contributing to development of the technology.

In addition, the particle control devices according to the embodiments of the present invention may be utilized in single-molecule detection techniques. Although different fields in biology currently require single-molecule image acquisition using an optical system, it may be quite difficult to acquire high quality still images despite an implementation of a high performance optical system due to Brownian motion of nanoparticles. To overcome the problem, the particle control devices according to the embodiments of the present invention are configured to acquire high quality still images by capturing a single molecule between electrodes and thus restricting the Brownian motion thereof. The particle control devices are also configured to detach captured nanoparticles by using a negative dielectrophoretic force for another process, thereby providing a new paradigm for biology-based single molecule detection.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A particle control device for controlling fine particles, the particle control device comprising:
    a base comprising a predetermined area and an insulator;
    a first electrode and a second electrode disposed on the base and separated from each other by a predetermined distance, wherein the first electrode comprises branch electrodes, wherein each branch electrode comprises a first end and a second end, and wherein at least two of the branch electrodes comprise first ends that are more densely arranged than their second ends; and
    a fluid flow path disposed on the base and disposed to pass between the first ends of the branch electrodes and the second electrode, and configured to allow a solution to flow;
    wherein fine particles that are disposed between the first electrode and the second electrode are controlled by a dielectrophoretic force disposed between the first electrode and the second electrode, the force controlling the fine particles by applying powers comprising different polarities to the first electrode and the second electrode.

2. The particle control device of claim 1, wherein the first electrode and the second electrode are separated from each other in a horizontal direction on a plane created by the base.

3. The particle control device of claim 1, wherein the base comprises a solution filling groove formed on the fluid flow path between the first electrode and the second electrode, and
    wherein at least a portion of the first end of each of the branch electrodes is disposed on the solution filling groove.

4. The particle control device of claim 1, further comprising:
    a cover glass disposed on the base and comprising a predetermined area,
    wherein the fluid flow path is formed by a space between an upper surface of the base and the cover glass.

5. The particle control device of claim 1, wherein at least two of the plurality of branch electrodes are bent or curved so that their first ends are densely arranged, and disposed proximate to the second electrode.

6. The particle control device of claim 1, wherein each of the branch electrodes comprises a tip at the first end, and
    wherein the tip has a fine width, and comprises a pin-like shape that extends towards the second electrode.

7. The particle control device of claim 1, wherein the width of the tip has a value in a range of about 1 nm to about 100 nm.

8. The particle control device of claim 1, wherein the first end is disposed closer to the second electrode than the second end is disposed in relation to the second electrode.

9. The particle control device of claim 1, wherein at least two of the branch electrodes are bent or curved so that their first ends are more densely arranged than their second ends.

10. The particle control device of claim 1, wherein each branch electrode further comprises a fine width.

* * * * *